(12) United States Patent
Hossainy et al.

(10) Patent No.: US 6,623,733 B1
(45) Date of Patent: Sep. 23, 2003

(54) METHODS FOR TREATMENT OF VASCULAR DISEASE AND DEVICE FOR PREPARATION OF AN AUTOLOGOUS COMPOSITION FOR TREATING VASCULAR DISEASE

(75) Inventors: Syed F. A. Hossainy, Fremont, CA (US); Jeffrey A. Steward, Lakewood, CO (US); Paul M. Consigny, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/893,022

(22) Filed: Jun. 27, 2001

(51) Int. Cl.⁷ .................. A61K 48/00; A61K 35/12; A01N 63/00; C12N 5/02
(52) U.S. Cl. ................ 424/93.21; 424/93.1; 424/520; 424/572; 435/325
(58) Field of Search ............... 424/93.21, 93.1, 424/520, 572; 435/325

(56) References Cited

U.S. PATENT DOCUMENTS

| | | | |
|---|---|---|---|
| 5,098,665 A | * | 3/1992 | Katschnig et al. |
| 5,372,945 A | | 12/1994 | Alchas et al. |
| 5,785,965 A | | 7/1998 | Pratt et al. |
| 5,866,167 A | * | 2/1999 | Van Bossuyt |
| 5,948,246 A | | 9/1999 | Zuk, Jr. |
| 5,968,066 A | | 10/1999 | Fogarty et al. |
| 6,008,328 A | * | 12/1999 | Hsu et al. |
| 6,045,565 A | | 4/2000 | Ellis et al. |

OTHER PUBLICATIONS

DW 1966–17786F, Feb. 1999, United States, Pierrel Spa.*

* cited by examiner

Primary Examiner—Christopher R. Tate
Assistant Examiner—Randall Winston
(74) Attorney, Agent, or Firm—Blakely, Sokoloff, Taylor & Zafman LLP

(57) ABSTRACT

A method for making a composition for administration to a patient, where the method includes: harvesting tissue including cells from a patient, lysing the cells to form a lysate, filtering the lysate to yield a filtrate, and collecting the filtrate as a composition comprising the filtrate for administration to said patient.

16 Claims, 1 Drawing Sheet

METHODS FOR TREATMENT OF VASCULAR DISEASE AND DEVICE FOR PREPARATION OF AN AUTOLOGOUS COMPOSITION FOR TREATING VASCULAR DISEASE

BACKGROUND OF THE INVENTION

1. Field of the Invention

The present invention involves a method of treating vascular disease through administration of an autologous angiogenic solution, and methods and devices for preparing such a solution.

2. Description of the Background

Localized hypoxia of tissue due to obstruction of the inflow of arterial blood (a form of vascular disease known as ischemia) leads to the secretion of chemicals from this tissue. These chemicals are often referred to as angiogenic factors. The secretion of angiogenic factors causes normally quiescent endothelial cells that line the blood vessels to become activated. The activated endothelial cells then release enzymes that degrade extracellular matrix barriers. Through proliferation and migration, the cells then form new vessels. The formation of new capillary blood vessels from a pre-existing vessel is known as "angiogenesis."

In patients afflicted with diminished coronary blood flow, ischemia in the area of the heart known as the myocardium is called "myocardial ischemia." Current research efforts for treating myocardial ischemia include injecting substances that promote angiogenesis into the myocardium of the patient. The therapeutic substances being investigated for such procedures include vascular endothelial cell growth factor (VEGF) and fibroblast growth factor (FGF). VEGF and/or FGF may be delivered to the myocardium by means of a catheter to the coronary arteries. Alternatively, the VEGF and/or FGF may be introduced through an open chest procedure.

Scientific literature available includes many articles that show the presence of VEGF and FGF promote angiogenesis. Recent review articles surveying the literature include: Ferrara, N., "Role of Vascular Endothelial Growth Factor in the Regulation of Angiogenesis" Kidney Int. 1999 September; 56(3) 794–814; Isner, J M "Vascular Endothelial Growth Factor: Gene Therapy and Therapeutic Angiogenesis" Am. J. Cardiol. 1998 November 19; 82(10A):63S–64S; Vlodavsky et al., "Extracellular Matrix-resident Basic Fibroblast Growth Factor; Implication For The Control of Angiogenesis", J. Cell Biochem. 1991 February; 45(2): 167–176; Klein et al., "Fibroblast Growth Factors As Angiogenesis Factors: New Insights Into Their Mechanism of Action", EXS. 1997; 79:159–192; Wilzenbichler B. et al., "Vascular Endothelial Growth Factor-C (VEGF-C/VEGF-2) Promotes Angiogenesis in the Setting of Tissue Ischemia" AM Pathol. 153: 381–394, 1998 (VEGF induces endothelial cell proliferation (EC50=1–10 ng/ml) and migration (EC= 0.1–1.0 ng/ml) in culture; Lopez J J et al., "VEGF Administration in Chronic Myocardial Ischemia in Pigs" Cardiovasc Res 40: 272–281, 1998 (In pigs, administration of 20 micrograms of VEGF delivered to the heart via intracoronary injection or epicardial implantation significantly increased myocardial blood flow and vasodilatory reserve compared to saline); Hendel R C et al., "Effect of Intracoronary Recombinant Human Vascular Endothelial Growth Factor on Myocardial Perfusion. Evidence for a Dose-Dependent Response" Circulation 101: 118–121, 2000 (In humans, single intracoronary injections of recombinanat human VEGF at concentrations of 0.005–0.167 micrograms/kg have been used in an attempt to induce myocardial angiogenesis); Kawasuji M. et al., "Therapuetic Angiogenesis with Intramyocardial Administration of Basic Fibroblast Growth Factor" Ann Thorac Surg 69: 115–1161, 2000 (In dogs, 100 micrograms of human recombinant bFGF injected into the myocardium at the time of LAD coronary artery ligation significantly increased capillary density and blood flow to the myocardium compared to the injection of saline); Laham R J. "Intrapericardial Delivery of Fibroblast Growth Factor-2 Induces Neovascularization in a Porcine Model of Chronic Myocardial Ischemia" J Pharmacol Exper Therap 292: 795–802, 2000 (In pigs with ameroid induced myocardial ischemia, a single intrapercardial injection of 200 micrograms bFGF increased angiographic collaterals and myocardial perfusion and function); and Unger EF et al. "Effects of a Single Intracoronary Injection of Basic Fibroblast Growth Factor in Stable Angina Pectoris" Am J Cardiol 85: 1414–1419, 2000 (In humans, single injections into the left main coronary artery of bFGF in doses ranging from 3 to 30 ug/kg were well tolerated).

Under a current treatment method, the VEGF and/or FGF are obtained from a xenogenic source (i.e., derived from a non-human animal, such as a pig or rabbit), or an allogenic source (i.e., derived from a human, but not the patient being treated). Insufficiently purified VEGF or FGF may result in an adverse patient reaction (e.g., infections, or immune system rejection) which destroys the "foreign" substance, as well as decreased potency of the VEGF or FGF. When administered directly to the myocardium (which is not well protected.by the immune system), insufficiently purified VEGF or FGF may result in myocardial cell necrosis due to the recruitment of neutrophils to the area, which can release potent free radicals and enzymes that can kill cells. Accordingly, many steps are required to complete separation of the VEGF or FGF from other proteins in the xenogenic or allogenic cells, and the potential for contamination must be dealt with at each step. Consequently, the process of purifying the VEGF or FGF from a xenogenic or allergenic source is very expensive. Moreover, there is a high probability of disease transfection to the patient, despite best efforts to limit contamination, since every animal and human carries a bacterial and viral population that is at least slightly different than that carried by the patient to be treated.

In accordance with another current treatment method, the VEGF or FGF is obtained from a genetically engineered source and then administered to the patient. For example, a bacterial culture may be stimulated to secrete VEGF or FGF by inserting porcine DNA fragments coding for VEGF or FGF into the DNA of the bacteria. As the bacteria reproduce, more VEGF and FGF can be produced. While this method may be less expensive than obtaining VEGF or FGF from xenogenic or allergenic sources, and may have a lower risk of disease transfection, the VEGF or FGF produced must still be separated from other compounds produced by the bacteria.

In accordance with yet another current method, gene therapy is used to cause the patient's own cells to produce VEGF or FGF. Gene therapy involves the injection of genetic material, known as deoxyribonucleic acid (DNA), into the patient. The DNA may be used directly, or packaged in an inactive virus, or in a liposome. The DNA so injected enters the nucleus of target cells (e.g., myocardial cells if treating myocardial ischemia) and causes the target cells to produce the protein dictated by the DNA sequence (in this case the DNA for VEGF or FGF). Angiogenesis will occur in those areas where the VEGF or FGF are found in a high enough concentration to elicit an effect and where the local cells are responsive to the stimulus (assuming VEGF or FGF are the only proteins required for angiogenesis).

However, the use of gene therapy to induce angiogenesis in a patient also has drawbacks. First, placing the DNA in the target cells is difficult. While conventional drugs work outside cell walls, the DNA must penetrate not only the cell wall, but also the nucleus within the cell. The fraction of cells that actually take up and express the new DNA is quite low, typically a few percent, and at best 10–20%. Secondly, the DNA that actually enters the cell nuclei may be attacked by the patient's immune system. When the immune system is activated in this manner, the immune system may also harm healthy genes in the target cells and in other nearby cells.

Thus, there is a clear need for a method of treating ischemia and other disorders associated with diminished blood flow that does not suffer from the disadvantages described above associated with non-autologous sources, genetic engineering, and gene therapy.

SUMMARY OF THE INVENTION

The present invention provides methods and apparatuses for obtaining compositions that may be used to treat ischemia and other forms of vascular disease and to increase circulation to tissue where blood flow is limited. The compositions are autologous, that is, derived directly from the patient to be treated, rather than from a xenogenic or allogenic source. Such autologous compositions will not be attacked by the patient's immune system. Moreover, since purification of the autologous composition is not required, potential costs associated with minimizing contamination during the purification process is avoided. The autologous composition, called the "autologous angiogenic product" herein, is believed to include numerous angiogenic factors, such as monobutryin, VEGF and FGF, that cause angiogenesis in ischemic tissue regions (e.g., regions of myocardial ischemia) or normal tissue regions bordering the ischemic regions when administered to the patient.

In accordance with one embodiment of a method of the present invention, an autologous angiogenic product for administration to a patient is obtained by harvesting cells from tissue of the patient; lysing the cells to form a lysate; filtering the lysate to yield filtrate having angiogenic components; and collecting the filtrate. The tissue may be perirenal adipose tissue that is harvested by, for example, a core biopsy needle. Alternatively, the tissue may be subcutaneous adipose tissue that is harvested by, for example, a liposuction-type device. As another alternative, the tissue may be a vein harvested by surgical removal.

The present invention also provides an apparatus for preparation of an autologous angiogenic product from tissue harvested from the patient. One embodiment of such an apparatus includes a lysing chamber, and a lysate collection and filtration chamber.

The lysing chamber includes an inlet for receiving autologous tissue; a lysing element for lysing the autologous tissue to produce a lysate; and an outlet for dispensing the lysate from the lysing chamber. The lysing element may be a metallic blade or an ultrasound transducer.

The lysate collection and filtration chamber, which receives the lysate produced in the lysing chamber, includes an upper reservoir; a lower reservoir; and a necking portion between the upper reservoir and the lower reservoir. The upper reservoir contains a fine particle filter for removing fine particles from the lysate. The lower reservoir receives the filtered lysate.

These and other features and aspects of the present invention will become more clear in view of the accompanying drawing and the following detailed description of the exemplary embodiments.

DETAILED DESCRIPTION OF THE EMBODIMENTS

Figure 1:
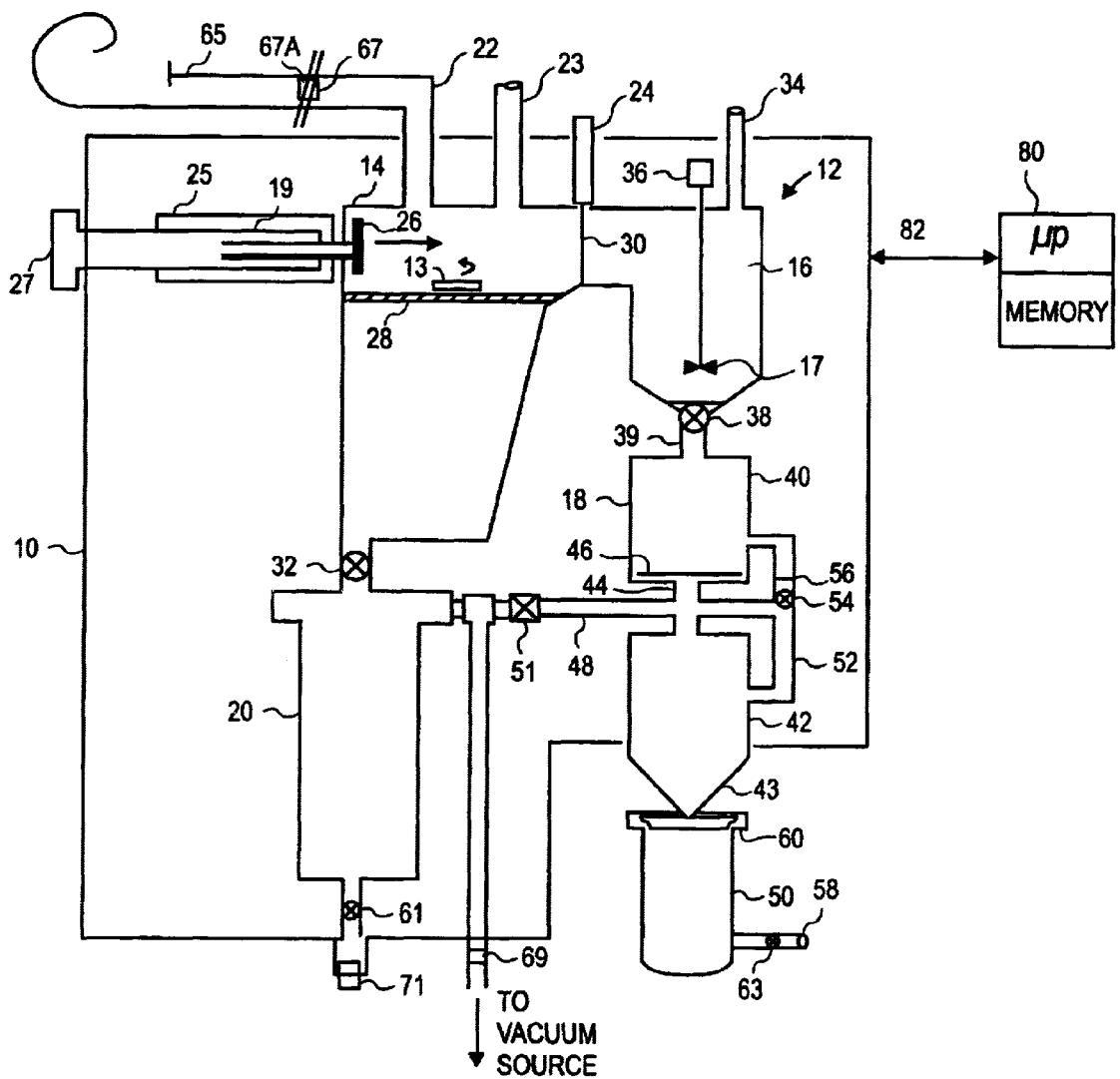
FIG. 1 is a schematic diagram of an exemplary apparatus for producing an autologous angiogenic product from tissue harvested from a patient's body.

The present invention includes methods for treating ischemia and other forms of vascular disease that involve administration of an autologous angiogenic composition to the patient and an exemplary apparatus for producing the autologous angiogenic product from the same patient's tissue.

In the discussion below, an embodiment of a method for treating vascular disease is described first, followed by a description of an apparatus which may be used in conjunction with this method. Then, a second embodiment of the method is described.

Method for Harvesting and Processing Patient Tissue to Yield an Autologous Angiogenic Product In a first embodiment, adipose tissue is harvested from the patient as a source of angiogenic factors. For example, perirenal adipose tissue may be harvested. Perirenal adipose tissue is believed to be particularly suitable for the present purposes because perirenal adipose tissue contains a higher concentration of angiogenic factors than does adipose tissue harvested from the omentum. An advantage of harvesting perirenal adipose tissue to obtain the autologous angiogenic product is that harvesting of perirenal adipose tissue does not require a penetration of the peritoneum. Hence, the harvesting step is significantly less invasive than it would be if adipose tissue from other locations was harvested.

Various methods may be used to harvest the perirenal adipose tissue. In one embodiment, the perirenal adipose tissue is harvested using a core biopsy needle (i.e., a very sharp, hollow needle). The core biopsy needle punctures the perirenal adipose tissue percutaneously. When the barrel of the needle is withdrawn, the core biopsy needle takes up a core of tissue. Useful biopsy needles and guns include the ASAP and TOP NOTCH automated core biopsy systems from Boston Scientific Corporation (Natick, Mass.) and the BioPince system from Amedic AB (Sollentuna, Sweden). If an 18-gauge needle is used, approximately 1–100 mg of perirenal adipose tissue may be harvested. Multiple biopsies may be required to harvest sufficient perirenal adipose tissue to supply a sufficient volume of angiogenic factors.

Alternately, subcutaneous adipose tissue may be harvested as a source of the angiogenic factors. In one embodiment, the subcutaneous adipose tissue is obtained by suction-assisted lipectomy, which is a conventional plastic surgery technique used to remove fat deposits. In such methods, a metal cannula with side holes is connected to a high-pressure vacuum. The vacuum draws fat deposits from, for example, the abdomen or thighs.

Alternately, a blood vessel could be harvested from the patient as a source of the angiogenic factors. For example, a vein may be harvested by a Vasoview Uniport™ endoscopic vessel harvesting system, manufactured by Guidant Corporation of Santa Clara, Calif.

Both liposuction of subcutaneous adipose tissue and removal of certain veins (e.g., varicose veins) are minimally traumatic procedures that may be performed while the patient is under a local anesthetic. Removal of perirenal adipose tissue is a more intrusive procedure. Accordingly, the patient's condition must be considered when selecting the tissue and harvesting methods to be used.

In accordance with this embodiment of the method, following harvesting of the tissue (which is composed of cells) from the patient, the cells are lysed to release their contents, yielding a lysate. A portion of the lysate includes angiogenic substances. The lysate is then filtered, yielding a filtrate. The filtrate is then collected and administered to the patient by one of several means. Further details regarding this embodiment of the method are provided below, in conjunction with the discussion of an apparatus suitable for preparing an autologous angiogenic product from harvested patient tissue.

Device for Preparing an Autologous Angiogenic Product From Harvested Patient Tissue FIG. 1 illustrates an embodiment of an apparatus useful for preparation of an autologous angiogenic product from tissue harvested from a patient. The apparatus is denoted herein as processing device 12. The embodiment of device 12 illustrated by FIG. 1 includes four primary subsystems: (1) a tissue isolation chamber; (2) a waste chamber; (3) a lysing chamber; and (4) a lysate collection and filtration chamber. A housing 10 encloses the various components of device 12. Housing 10 serves to make device 12 easier to handle, while keeping the internal portions of device 12 sterile. Housing 10 may be made from a material that is lightweight, inert, and easy to sterilize (e.g., polycarbonate, polypropylene, or polyethylene).

In one embodiment, the operations and subsystems of device 12 are controlled by a controller 80, which communicates operational instructions and receives data from device 12 over bus line 82. Typically, controller 80 includes a microprocessor for the controlling function and a memory for storing instructions and data. In an alternative embodiment, controller 80 may be within housing 10.

As a first step in the preparation of an autologous angiogenic product, harvested tissue is introduced from harvesting device 65 into device 12 at inlet 22. Airtight fitting 67 is provided at the end of inlet 22. The tissue harvesting device 65 is attached to the proximal portion 67A of airtight fitting 67. Inlet 22 may be constructed of, for example, polymethylmethacrylate or plexiglass. Inlet 22 should be constructed so as to permit the harvested tissue to be introduced from an external tissue harvesting device 65 directly into tissue isolation chamber 14 under sterile conditions. Tissue harvesting device 65 may be, for example, a modified liposuction device, or a modified endoscopic vessel harvesting device, such as the Vasoview Uniport™ endoscopic vessel harvesting system, commercially available from Guidant Corporation of Santa Clara, Calif. In tissue isolation chamber 14, patient fluids (e.g., blood, peritoneal fluid) that have been entrained with the harvested tissue are removed by rinsing.

After the harvested tissue is introduced to tissue isolation chamber 14, the operator may also introduce a rinse solution (e.g., saline, phosphate-buffered saline (PBS) or some other physiological buffered solution) through inlet 22 or a second inlet 23 to assist in filtration. When isolation valve 32 (e.g., a ball valve or gate valve) is opened, and a vacuum or suction is exerted on vacuum or suction line 48 by a vacuum or suction source (not shown), patient fluids and rinse solution are pulled through the openings in filter 28 and into waste chamber 20, which collects waste materials produced during the rinsing process. Filter 28 may have an opening size of, for example, 10 $\mu$m to 100 $\mu$m. Intact harvested tissue is thereby retained above filter 28. The harvested tissue may be more effectively rinsed if a magnetic stirrer 13 is used in conjunction with filter 28, so as to prevent the harvested tissue from forming a bed of material within tissue isolation chamber 14. Airtight fitting 71 may be used to selectively drain waste solution contained in waste chamber 20 to an appropriate receptacle for subsequent disposal.

Tissue isolation chamber 14 also includes a plunger 26 and a movable plate 30, which is preferably vertically movable. Plunger 26 and plate 30 are used to remove fluid from harvested tissue. Plunger 26 is part of a cylinder 25 having a barrel 19 and a handle 27. Handle 27 may be disposed outside housing 10 of device 12, and may be pneumatically activated. When handle 27 is pushed forward, plunger 26 moves axially forward to move the harvested tissue against plate 30. This force expels fluid from the harvested tissue. Movement of plunger 26 toward plate 30 may be repeated, if desired, to enhance removal of fluid from the harvested tissue. After sufficient rinsing and isolation of tissue, plate 30 is raised or otherwise opened by separator 24, which may be a pneumatically activated cylinder, to allow the processed tissue (which is essentially a slurry because it still contains solid matter) to enter lysing chamber 16. Separator 24 thus controls fluid communication between tissue isolation chamber 14 and lysing chamber 16.

Plunger 26 may be made from polytetrafluoroethylene (e.g., Teflon®), while plate 30 may be made from stainless steel. In any event, the materials selected for plunger 26 and plate 30 should be inert and durable.

One of ordinary skill in the art will appreciate that other means besides tissue isolation chamber 14 could be used within device 12 to isolate harvested tissue from patient fluids. For example, in another embodiment, a porous tumbling vessel having inlets similar to inlets 22 and/or 23 is used instead of tissue isolation chamber 14. In such an embodiment, pores on the side of the tumbling vessel are of similar size to the openings in filter 28 of FIG. 1. The contents of the tumbling vessel would be transferred through the pores into lysing chamber 16, obviating the need for filter 28 and separator 24. Of course, tumbling of the harvested tissue must be performed under sterile conditions.

In lysing chamber 16, the processed tissue is further treated physically and/or chemically to cause the release of angiogenic factors from the cells which make up the processed tissue. Lysing chamber 16 includes an opening (created by lifting plate 30 vertically in this embodiment) for receiving the processed tissue, a lysing element 17, and an outlet 39 for dispensing the resulting lysate to lysate collection and filtration chamber 18.

Lysing element 17 physically lyses the cells that make up the processed tissue, and is powered by power source 36. Physically lysing the cells releases angiogenic factors and pro-inflammatory factors from the cells which are associated with new capillary growth. According to one embodiment of the present invention, lysing element 17 is a rotating blade made from, for example, stainless steel or glass. In this case, the rotating blade should be sized so as to provide adequate clearance from the walls of lysing chamber 16 during operation.

In another embodiment, lysing element 17 is an ultrasonic transducer. An ultrasonic transducer can be operated to generate a high frequency sound wave that physically disrupts cell membranes, causing the cells to lyse. The ultrasonic transducer may be operated at frequencies ranging from about 20 kHz to about 500 kHz to lyse the cells. The ultrasonic transducer may be made from many different materials, including for example, a ceramic material. To obtain low frequency vibration (i.e., around 20 kHz), the transducer should be about 1 inch in diameter and have a maximum length of 1.5 inches. If a transducer is used as lysing element 17, then lysing chamber 16 should be saturated with fluid (i.e., no air present within lysing chamber 16) before the transducer is activated. Otherwise, ultrasound waves delivered by the transducer will be reflected by the air, and thus the cells may not lyse. Of course, other means of physically lysing the cells are also possible.

An outlet 39 is provided for draining the lysate from lysing chamber 16. In one embodiment, a valve 38 selectively controls fluid communication between outlet 39 of lysing chamber 16 and lysate collection and filtration chamber 18.

In addition to physically lysing, other steps may be performed in lysing chamber 16 to treat the processed tissue. For example, in the embodiment illustrated in FIG. 1, inlet 34 is provided to allow the introduction of a treatment substance. A volume of digestive enzyme solution, such as collagenase, or other tissue dissociation enzyme, may be introduced through inlet 34 before lysing, causing the tissue mass to disperse and produce a tissue digest. For example, a solution is prepared including type I collagenase (4 mg/mL) and serum albumin (4 mg/mL) in calcium and magnesium free Dulbecco's phosphate buffered saline. The solution may then be warmed to 37° C., for increased activity of the collagenase enzyme. A volume of this solution equal to the volume of tissue present in lysing chamber 16 is introduced through inlet 34. Trypsin (0.1% solution) or possibly elastase could also be used instead of collagenase.

Alternately, autologous cells, such as leucocytes, monocytes or autologous blood platelets, may be added to the lysing chamber 16 through inlet 34. When such autologous cells or blood platelets are lysed by lysing element 17, chemicals that promote angiogenesis are released by the autologous cells or blood platelets.

In another embodiment, autologous progenitor cells (e.g., stem cells or endothelial cell progenitors) are introduced into lysing chamber 16 through inlet 34 after lysing is performed. The progenitor cells may be harvested from the patient's circulatory system or from the patient's bone marrow using known techniques. In the environment of the angiogenic filtrate (obtained at lower reservoir 42 as described below), the progenitor cells could convert into an endothelial cell type. This conversion presumably involves stimulation of the progenitor cells by angiogenic factors in the filtrate, which initiate internal cell signaling processes. The cell signaling processes ultimately result in a change in gene expression that converts the cell from a progenitor cell to an endothelial cell. Therefore, in this embodiment, the autologous angiogenic product includes endothelial cells which can serve as the original material for new capillaries.

In another embodiment, the autologous progenitor cells are lysed in lysing chamber 16. Upon lysing, the autologous progenitor cells will release substances, such as growth factors and cytokines, that promote angiogenesis.

In yet another embodiment, a biological factor is introduced to lysing chamber 16 at inlet 34 after lysing is performed. For example, monocyte chemoattractant protein-1 (MCP-1) may be added to the lysate. MCP-1 increases the recruitment of macrophages to the region where MCP-1 is administered in a patient. Macrophages are thought to release growth factors (e.g., platelet-derived growth factor), cytokines (interleukin-1, tumor necrosis factor) and matrix degrading enzymes (metalloproteinases such as MMP-2, MMP-9) that promote angiogenesis. MCP-1 can be obtained from the patient's own cells (after an extensive protein purification process) or is commercially available from genetic engineering supply houses.

In yet another embodiment, a pro-angiogenic substance is introduced to lysing chamber 16 at inlet 34 after lysing is performed. The substance may be encapsulated in a microsphere, a liposome or a hydrogel. Of course, adding non-autologous materials, as may occur in the latter two embodiments, can reduce the effectiveness of the autologous angiogenic product.

After the lysate is produced in lysing chamber 14, and other substances are introduced to the lysing chamber (if desired), the lysate is received and filtered by lysate collection and filtration chamber 18. Lysate collection and filtration chamber 18 includes an upper reservoir 40, a lower reservoir 42, and a necking portion 44 disposed between upper reservoir 40 and lower reservoir 42. When valve 38 is opened, upper reservoir 40 receives the lysate produced in lysing chamber 16. A fine particle filter 46 is disposed within upper reservoir 40. Fine particle filter 46 may be, for example, a standard syringe filter made from polytetrafluoroethylene (e.g., Teflon®) or nylon. A uniform opening size of fine particle filter 46 may range from about 0.1 $\mu$m to about 0.5 $\mu$m.

Necking portion 44 of lysate collection and filtration chamber 18 is in fluid communication with vacuum or suction line 48. Vacuum or suction line 48 includes a valve 51, which is in fluid communication with a vacuum or suction source (not shown). When opened, valve 51 permits the vacuum or suction source (which may be external to housing 10) to exert a vacuum or suction on upper reservoir 40. The vacuum or suction draws the lysate through fine particle filter 46 and into lower reservoir 42, thereby producing a filtered lysate. Of course, the amount of vacuum or suction exerted by the vacuum or suction source should not be so high as to draw the filtered lysate into vacuum or suction line 48. Isolation valves 32, 38, and 61 are typically closed when performing this filtration step. Vacuum or suction line 48 should be constructed from materials having sidewalls that will not collapse under the force of the applied vacuum or suction and is easily cleaned (e.g., stainless steel).

According to the above-described operation of filter 46, a finely filtered autologous solution (i.e., the autologous angiogenic product) containing various angiogenic factors collects in lower reservoir 42.

The presence of some cell debris in the angiogenic solution may result in greater production of macrophages and monocytes, resulting in a solution with a higher concentration of angiogenic factors. Accordingly, to provide a path for introduction of such optional cell debris, fine particle filtration chamber 18 further includes a bypass line 52, the entrance to which is disposed above fine particle filter 46. Bypass line 52 includes a valve 54. Opening valve 54 permits some of the cellular debris suspended in the lysate in upper reservoir 40 to pass to lower reservoir 42.

Bypass line 52 is further provided with a filter 56 upstream of valve 54 to better control the size of debris that pass to lower reservoir 42. Usefully, filter 56 has openings sized about one order of magnitude greater than the openings in particle filter 46. Thus, for example, if fine particle filter 46 has an opening size of 0.1 microns, then filter 56 would have an opening size of 1.0 microns. In any event, the opening size for filter 56 should be selected such that cell debris passed to the autologous angiogenic product in lower reservoir 42 is not so large as to present the risk of an embolism when administered to the patient.

In one embodiment, lysate collection and filtration chamber 18 is modular and easily removable from isolation valve 38 and isolation valve 51 so that it may be easily sterilized and re-used after the procedure is completed.

In another embodiment, lysate collection and filtration chamber 18 and bypass line 52 are easily removable from isolation valve 38 and isolation valve 51 and are also disposable.

Collection vial 50 is provided for sterile collection of and transfer of the autologous angiogenic product. Collection vial 50 is positioned so as to be in fluid communication with lower reservoir 42. Collection vial 50 is provided with a rubber septum 60, in a manner similar to those provided on vials that hold blood samples. Rubber septum 60 is penetrated by tip 43 of lower reservoir 42. Tip 43 includes an orifice through which the autologous angiogenic product is transferred from lower reservoir 42 to collection vial 50. In one embodiment, an in-line bubble detector is used to sense the height of the autologous angiogenic product as it collects in collection vial 50.

In one embodiment, collection vial 50 is sized and built so as to be easily removed from lower reservoir 42 and placed on a syringe, while maintaining sterile conditions. With the collection vial 50 connected to a syringe with the appropriately sized needle, the autologous angiogenic product can be injected directly into any tissue for treatment of an ischemic condition. Such tissues include, but are not limited to: normal tissue adjacent to ischemic tissue, ischemic tissue (e.g., ischemic coronary tissue), a blood vessel supplying blood flow to the ischemic tissue, and the periadventitial space around a blood vessel supplying blood flow to the ischemic tissue. Administration of an autologous angiogenic product to an ischemic organ can be done by an open surgical procedure. In other cases, administration may be performed using a syringe, including a syringe mounted on an intravascular catheter.

In another embodiment, collection vial 50 is sized and built so as to be easily removed from lower reservoir 42 and placed on an interventional device (e.g., a catheter) under sterile conditions. The delivery of autologous angiogenic product may be coupled with other synergistic drugs using, for example, a catheter.

Collection vial 50 may further include a sampling port 58. A valve 63 permits selective fluid communication prior to administration to the patients between sampling port 58 and collection vial 50. Accordingly, a sample of the autologous angiogenic product may be easily collected prior to administration to the patient. Subsequent chemical analyses of such samples can be performed to determine both the components contained in the autologous angiogenic product, and the concentration of those components (e.g., an enzyme-linked immunosorbent assay (ELISA), which is capable of measuring less than a nanogram of a protein). Thus, quality control may be exercised over the administration of autologous angiogenic product to the patient, ensuring that angiogenic factors such as monobutryin, VEGF and/or FGF are present at therapeutic levels in the autologous angiogenic product.

Examples of commercially available products include the Quantikine human VEGF immunoassay, Catalog number DVE00, and Quantikine human FGF basic immunoassay, Catalog number DFB50, both available from R and D Systems Inc., Minneapolis, Minn. These assays employ the quantitative sandwich enzyme immunoassay technique. A monoclonal antibody specific for human VEGF or bFGF is precoated onto a microplate. Standards and samples are pipetted into the wells of the microplate and any VEGF or bFGF present is bound by the immobilized antibody. After washing away any unbound substances, an enzyme-linked polyclonal antibody specific for VEGF or bFGF is added to the wells. Following a wash to remove any unbound antibody-enzyme reagent, a substrate solution is added tot he wells and color intensity develops in proportion to the amount of VEGF or bFGF bound in the initial step. Color development is stopped and the intensity of the color is measured using a microplate spectrophotometric reader.

Tissue isolation chamber 14, described earlier in this section, is not a necessary element of device 12, in that patient fluids which are removed from the tissue by tissue isolation chamber 14 may potentially also contain angiogenic components. Thus, in another embodiment of the apparatus, no tissue isolation chamber 14 or waste chamber 20 is present, and harvested tissue is introduced directly to lysing chamber 16. However, tissue isolation chamber 14 is useful to have as a first operation in the process of obtaining an autologous angiogenic product, so that the remaining steps in the process can be completed more quickly.

Elements of device 12 external to housing 10 include portions of inlets 23 and 34, separator 24, and tip 43 of the lower portion 42 of lysate collection and filtration chamber 18. Airtight fitting 71 may be used to drain waste solution contained in waste chamber 20 to an appropriate receptacle for subsequent disposal. Airtight fitting 69 is used to connect vacuum or suction line 48 to a vacuum or suction source (e.g., a vacuum pump). Handle 27 of syringe 25 may also be external to housing 10. The autologous angiogenic product is collected from lower reservoir 42 using sterile transfer techniques, and subsequently is available for injection into the patient from whom the tissue was harvested without further processing. Advantageously, the angiogenic filtrate is a cocktail of autologous components, including FGF, VEGF, and other promoters of angiogenesis that may be derived from human tissue. Moreover, assuming the angiogenic filtrate is fully autologous, then the angiogenic filtrate should not evoke an immune system response in the patient. Between about 0.1 mL and about 5.0 mL of the autologous angiogenic product is preferably produced and injected into the myocardium to stimulate angiogenesis in the ischemic myocardium of a patient.

Advantageously, since the angiogenic product is autologous, the primary potential sources of contamination of the angiogenic product are the tissue harvesting device 65 and device 12. Therefore, tissue harvesting device 65 and device 12 should be sterilized before each use by, for example, autoclaving. Sterile transfer technique should be observed when delivering harvested tissue from tissue harvesting device 65 to inlet 22 of device 12. The potential for contamination from device 12 can be reduced by, for example, minimizing surface area to volume ratios in the various chambers to minimize deposition of airborne contaminants.

Moreover, device 12 permits the sterile collection, containment and processing of tissue harvested from the patient, to yield an autologous angiogenic product, while minimizing operator handling, and thus the potential for contamination.

Method for Inducing an Inflammatory Response to Yield an Autolopous Angiogenic Product According to another embodiment of the method of the present invention, an autologous angiogenic product is produced by inflaming a selected subcutaneous region of the patient, thereby inducing an inflammatory response. The selected subcutaneous region may be inflamed by injection of non-proteinaceous, non-cell-derived foreign bodies into internal tissues. For example, absorbable glass particles (e.g., Bioglass®, a silica glass commercially available from US Biomaterials, Gainesville, Fla.) or high molecular weight absorbable polymeric particles (e.g., poly-lactic acid (PLA) or polycaprolactone (PCL)) could be injected subcutaneously, at the patient's forearm, thigh, or buttocks, for example. Between about 10 $\mu$g and 200 $\mu$g of particles could be injected per square centimeter of the subcutaneous region selected.

In response to the injection of these foreign bodies,-an inflammatory response fluid (i.e., the autologous angiogenic product containing angiogenic factors, such as VEGF and FGF) would gather at the site of inflammation within one to four days. The inflammatory response fluid at the site of inflammation is subsequently withdrawn, collected, and administered to the patient. The inflammatory response fluid may be withdrawn, for example, by a syringe through a needle or a catheter attached to the syringe. The absorbable glass or polymeric particles would harmlessly degrade in the body thereafter. Advantageously, this method likewise provides an autologous angiogenic product which may be collected and provided to the patient without purification, with only minimal opportunity for contamination.

According to another embodiment of the method, a pro-inflammatory or inflammatory agent is delivered to the selected subcutaneous region. The inflammatory chemical could be, for example, thioglycolate, which is used to elicit macrophage recruitment in animals; MCP-1, a stimulant of macrophage recruitment; tumor necrosis factor alpha (TNF α); interleukin 1 beta, lipopolysaccharide, or interleukin 6, among other possibilities. These compounds are proteinaceous or cell derived and induce an inflammatory response based on their biologic ability to bind to specific receptors that induce cells to release pro-inflammatory factors. As in the embodiment described above, inflammatory response fluid is withdrawn from the inflamed subcutaneous region, and then administered to the patient.

In accordance with another embodiment of the method, an adjuvant is administered in conjunction with the inflammatory chemical. Adjuvants are chemicals which may be used to amplify an inflammatory reaction. Such adjuvants would include aluminum hydroxide, Elvax™ (an ethylene-vinyl acetate copolymer), L-tyrosine, and nitrocellulose, among other possibilities. As an example, nitrocellulose might be subdermally injected along with MCP-1 in a selected region of the patient, thereby increasing the duration of release of MCP-1, and amplifying the inflammatory reaction.

In accordance with another embodiment of the method, a bruise is inflicted on the patient by, for example, a spring loaded piston, which strikes the skin with a known amount of force. An inflammatory reaction results, and inflammatory response fluid is collected from the inflamed area.

Regardless of the method chosen for production of the autologous angiogenic product, it should be appreciated that the autologous angiogenic product is useful not only for treating myocardial ischemia, but for treating the symptoms or reversing the progression of other forms of vascular disease, such as infarction, peripheral artery disease, intermittent claudication, and critical limb ischemia.

Methods of Administratiin of Autolopous Angiogenic Product

The autologous angiogenic product may be administered to the patient according to conventional practices. For example, in the context of myocardial ischemia, the autologous angiogenic product may be administered to the ischemic tissue by a syringe and needle or catheter, or to healthy tissue bordering the ischemic tissue, during an open chest procedure. Alternatively, a catheter equipped with a syringe may be used for such delivery.

While particular embodiments of the invention have been shown and described, it will be obvious to those skilled in the art that the invention is not limited to these embodiments of apparatuses and methods, and that modifications, combinations, and substitutions can be made without departing from the inventive concepts disclosed herein. Therefore, the appended claims are to encompass within their scope all such changes and modifications as fall within the scope of this invention.

What is claimed is:

1. A method comprising:
   harvesting tissue comprising cells from a patient, wherein said cells comprise angiogenic components;
   lysing the harvested tissue to form a lysate;
   filtering the lysate to yield a filtrate, the filtrate comprising said angiogenic components; and
   collecting said filtrate for administration to the patient.

2. The method of claim 1, wherein said tissue is selected from the group consisting of perirenal adipose tissue, subcutaneous adipose tissue, and a vein.

3. The method of claim 2, wherein said tissue comprises perirenal adipose tissue.

4. The method of claim 3, wherein said tissue is harvested using a core biopsy needle.

5. The method of claim 1, further comprising:
   removing patient fluids from said tissue.

6. The method of claim 5, wherein said removing patient fluids comprises rinsing said tissue.

7. The method of claim 1, further comprising introducing at least one of a pro-angiogenic factor and a biological factor to said lysate, after said lysing said cells.

8. The method of claim 1, wherein said filtering is accomplished using a filter comprising an opening size between about 0.1 $\mu$m to about 0.5 $\mu$m.

9. The method of claim 1, further comprising bypassing a portion of said lysate around said filtering.

10. The method of claim 9, further comprising filtering said bypass portion in a filter having an opening size between about 1.0 $\mu$m to about 5.0 $\mu$m.

11. The method of claim 1, further comprising depositing said filtrate in a collection vial.

12. The method of claim 1, comprising:
   adding a material selected from the group consisting of autologous cells, leucocytes, monocytes, and autologous blood platelets to said patient cells prior to said lysing.

13. The method of claim 1, further comprising:
   adding a substance selected from the group consisting of autologous progenitor cells, stem cells, and endothelial cell progenitors to said lysate.

14. The method of claim 1, further comprising:
   adding a substance selected from the group consisting of autologous progenitor cells, stem cells, and endothelial cell progenitors to said patient cells prior to said lysing.

15. The method of claim 1, further comprising:
   adding a substance selected from the group consisting of biological factors, monocyte chemoattractant protein-1 (MCP-1), macrophages, cytokines, interleukin-1, tumor necrosis factor, matrix degrading enzymes, metalloproteinases, MMP-2, and MMP-9 to said lysate.

16. The method of claim 1, further comprising adding a pro-angiogenic substance to said lysate, wherein said pro-angiogenic substance is encapsulated in a form selected from the group consisting of a microsphere, a liposome, and a hydrogel.

* * * * *

UNITED STATES PATENT AND TRADEMARK OFFICE
CERTIFICATE OF CORRECTION

PATENT NO. : 6,623,733 B1
DATED : September 23, 2003
INVENTOR(S) : Hossainy et al.

It is certified that error appears in the above-identified patent and that said Letters Patent is hereby corrected as shown below:

Column 12,
Line 13, after "A method," please insert -- for making a composition for administration to a patient, the method --.
Line 19, please delete "collecting said filtrate for administration to the patient" and insert -- collection said filtrate, wherein the composition comprises the filtrate for administration to said patient --.
Line 43, after "claim 1," please insert -- further --.
Lines 46 and 54, please delete "patient cells" and insert -- harvested tissue --.

Signed and Sealed this

Sixth Day of April, 2004

JON W. DUDAS
*Acting Director of the United States Patent and Trademark Office*